United States Patent
Cunningham et al.

(10) Patent No.: US 9,804,171 B2
(45) Date of Patent: Oct. 31, 2017

(54) DIAGNOSTIC METHOD FOR PEDIATRIC ACUTE-ONSET NEUROPSYCHIATRIC SYNDROME (PANS) AND PEDIATRIC AUTOIMMUNE NEUROPSYCHIATRIC DISORDER ASSOCIATED WITH STREPTOCOCCI INFECTION (PANDAS)

(71) Applicants: Moleculera Labs, Inc., Oklahoma City, OK (US); The Board of Regents of the University of Oklahoma, Norman, OK (US); National Institutes of Health, Bethesda, MD (US)

(72) Inventors: Phina Madeleine Cunningham, Oklahoma City, OK (US); Craig David Shimasaki, Edmond, OK (US); Susan E. Swedo, McLean, VA (US); Christine Kirvan, Lincoln, CA (US)

(73) Assignees: The Board of Regents of the University of Oklahoma, Norman, OK (US); Moleculera Labs, Inc., Oklahoma City, OK (US); National Institutes of Health, Bethsesda, MD (US)

( * ) Notice: Subject to any disclaimer, the term of this patent is extended or adjusted under 35 U.S.C. 154(b) by 22 days.

(21) Appl. No.: 15/045,146

(22) Filed: Feb. 16, 2016

(65) Prior Publication Data

US 2016/0161497 A1    Jun. 9, 2016

Related U.S. Application Data

(63) Continuation of application No. 14/790,416, filed on Jul. 2, 2015, which is a continuation of application No. 14/209,493, filed on Mar. 13, 2014, now abandoned.

(60) Provisional application No. 61/787,919, filed on Mar. 15, 2013.

(51) Int. Cl.
*A61K 38/00* (2006.01)
*G01N 33/53* (2006.01)
*G01N 33/68* (2006.01)
*G01N 33/564* (2006.01)
*G01N 33/569* (2006.01)

(52) U.S. Cl.
CPC ......... *G01N 33/686* (2013.01); *G01N 33/564* (2013.01); *G01N 33/56944* (2013.01); *G01N 33/6854* (2013.01); *G01N 33/6896* (2013.01); *G01N 2333/315* (2013.01); *G01N 2333/726* (2013.01); *G01N 2333/912* (2013.01); *G01N 2405/10* (2013.01); *G01N 2469/20* (2013.01); *G01N 2800/26* (2013.01); *G01N 2800/28* (2013.01); *G01N 2800/30* (2013.01); *G01N 2800/38* (2013.01)

(58) Field of Classification Search
None
See application file for complete search history.

(56) References Cited

U.S. PATENT DOCUMENTS

2013/0183680 A1    7/2013  Naides et al.

OTHER PUBLICATIONS

Schott et al. "Is there an immunopathology of the serotonergic synapse in mental disorder? Immunological alterations in psychiatric diseases." Advances in Biol Psych, vol. 18, 13-16, 1997.
Moleculera Labs, Inc. Cunningham Panel., pp. 1-7. Aug. 28, 2013.
International Search Report for PCT/US2014/047189, dated Nov. 28, 2014.

*Primary Examiner* — Olga N Chernyshev
(74) *Attorney, Agent, or Firm* — Knobbe Martens Olson & Bear LLP

(57) ABSTRACT

The present invention provides a panel of at least five clinical analyses or tests (using serum samples) to determine the risk of pediatric acute-onset neuropsychiatric syndrome (PANS) and/or pediatric autoimmune neuropsychiatric disorder associated with streptococcal infection (PANDAS) in an individual. These include enzyme linked immunosorbent assays (ELISAs) to measure antibody titers against neuronal antigens present in the brain; the neuronal antigens include lysoganglioside, tubulin, dopamine receptor D1, dopamine receptor D2, serotonin receptor 5HT2A, and serotonin receptor 5HT2C. Antibody titers against at least four of these neuronal antigens are required in the present methods; preferably antibody tiers against all of these neuronal antigens are measured. A final assay is used to quantify calcium/calmodulin-dependent protein kinase activity using a neuronal cell line. The results of these analyses or tests are then combined using an algorithm to determine whether a PANS or PANDAS diagnosis is appropriate for the individual. Depending on the diagnosis, an appropriate treatment can be determined.

14 Claims, 3 Drawing Sheets

DIAGNOSTIC METHOD FOR PEDIATRIC ACUTE-ONSET NEUROPSYCHIATRIC SYNDROME (PANS) AND PEDIATRIC AUTOIMMUNE NEUROPSYCHIATRIC DISORDER ASSOCIATED WITH STREPTOCOCCI INFECTION (PANDAS)

RELATED APPLICATIONS

This application claims the benefit and priority to and is a continuation of U.S. application Ser. No. 14/790,416, filed Jul. 2, 2015, which is a continuation of U.S. application Ser. No. 14/209,493, filed Mar. 13, 2014, which is based on, and claims the benefit of priority to, U.S. Provisional Application 61/787,919 filed on Mar. 15, 2013, which is hereby incorporated by reference.

BACKGROUND OF THE INVENTION

Field of the Invention

The present invention provides a convenient and accurate diagnostic method for pediatric acute-onset neuropsychiatric syndrome (PANS) and pediatric autoimmune neuropsychiatric disorder associated with streptococci infection (PANDAS). The ability to reliably diagnose PANS and/or PANDAS using such a method allows treating clinicians to prescribe treatments in a more effective and timely manner than currently possible. Such ability to reliably diagnose PANS and PANDAS is expected to allow significant improvement in the outcomes of many patients with PANS and/or PANDAS.

Description of the Related Art

Pediatric autoimmune neuropsychiatric disorder associated with streptococci infection (PANDAS) is a sudden and severe onset obsessive-compulsive disorder (OCD) or tic disorder described in 1998 (Swedo et al., Am. J. Psychiatry 155:2, 264-271 (1998)). Such disorders generally have an onset between the ages of about 2 to 14. There are currently five diagnostic criteria required for a PANDAS diagnosis:

(1) presence of OCD or tic disorder;
(2) prepubertal symptom onset;
(3) acute symptom onset and episodic (relapsing-remitting) course;
(4) temporal association of Group A streptococcal infection and symptom onset/exacerbations; and
(5) association with neuropsychiatric abnormalities (especially hyperactivity and choreiform movements). Swedo et al., Pediatr. Therapeut. 2012, 2:2.

More recently, pediatric acute-onset neuropsychiatric syndrome (PANS) has been described based on three diagnostic criteria:

(1) abrupt, dramatic onset of obsessive-compulsive disorder or severely restricted food intake;
(2) concurrent presence of additional neuropsychiatric symptoms, with
similarly severe and acute onset, from at least two of the following seven categories:
  (a) anxiety;
  (b) motional lability and/or depression;
  (c) irritability, aggression and/or severely oppositional behaviors;
  (d) behavioral (developmental) regression;
  (e) deterioration in school performance;
  (f) sensory or motor abnormalities; or
  (g) somatic signs and symptoms, including sleep disturbances, enuresis or urinary frequency; and (3) symptoms not better explained by a known neuropsychiatric or medical disorder (e.g., Sydenham chorea, systemic lupus erythematosus, Tourette disorder or the like). Id. Generally PANDAS, which has a temporal association of Group A streptococcal infection, is a subset of the more general PANS condition.

Some of most striking aspects of PANS/PANDAS include its rapid onset and the severity and variability of its neuropsychiatric abnormalities. Many parents can point to a particular day or week when the condition began, often describing the event as "falling off a cliff" or the "day they lost their child." A recent posting from the International OCD Foundation described the PANDAS experience as follows:

'My child was fine last week, last month—and now I have lost her. This is not my child; what has happened??? What do I do??'

"For every parent of a child with an illness, especially a mental illness, there is a particular story. But when you meet a parent of a child with PANDAS (typically a child between ages 3-14), you will hear the same panicked story over and over. A child who was happy at home and at school, and was social and athletic, is now walking in circles for hours, washing hands until they bleed, asking the same questions over and over—and over. A child that used to be comforted by a hug is now inconsolable. They may be begging parents for help, begging for a way to end the horror that exists only in their minds. Imagine a child screaming in terror in a corner, and a parent unable to hold them. These parents will tell you in detail about the day or week that their child changed. Here is what life looks like now—children may exhibit some or all of these symptoms:

Acute sudden onset of OCD
Challenges with eating, and at the extreme end, anorexia
Sensory issues such as sensitivity to clothes, sound, and light
Handwriting noticeably deteriorates
Urinary frequency or bedwetting
Small motor skills deteriorate—a craft project from yesterday is now impossible to complete . . .
Tics
Inattentive, distractible, unable to focus and has difficulties with memory
Overnight onset of anxiety or panic attacks over things that were no big deal a few days ago, such as thunderstorms or bugs
Suddenly unable to separate from their caregiver, or to sleep alone
Screaming for hours on end
Fear of germs and other more traditional-looking OCD symptoms"

"You will often find these parents on the computer every night, desperate for an explanation that makes sense. They are seeking specialists who can help—and finding no answers. They are starting to feel crazy themselves, because no one seems to believe what they are going through." Jenike and Dailey, International OCD Foundation (2012).

Thus, parents turning to the medical community are often at a loss since currently there are no clinical methods or tests to provide or confirm a diagnosis. Currently, only diagnosis based on existing observational clinical criteria are possible. Children presenting with neuropsychiatric symptoms would not generally be considered candidates for the most aggressive treatment options (e.g., autoimmune therapeutics or immune modulation treatments discussed below) without a diagnostic tool that shows autoimmune results. This is why there is significant difficulty in making a PANDAS/PANS diagnosis based upon symptoms alone; indeed, there is even difficulty in agreeing upon standard nomenclature for such conditions.

Effective treatments for PANDAS/PANS are available. During the early stages with bacterial infections, antibiotic therapy, perhaps even for several months, is recommended. Antibiotics (e.g., amoxicillin, penicillin, azithromycin, and cephalosporins) can be used to treat the strep infection in PANDAS and often result in immediate improvement. Treatment with other anti-infective agents may also be useful in some cases depending on the specific infection observed in particular cases. For purposes of this invention, antibiotic therapy is to include treatment with both antibiotics and other anti-infective agents.

Treatment with anti-inflammatory agents (including both steroids and non-steroidal anti-inflammatory drugs (NSAIDS)) may also be helpful. Treatment with prednisone or corticosteroids has been used with some reports of improvements. In some cases, however, tic conditions have actually worsened. Such treatments can only be used for short time periods due to possible serious long-term complications. And even where improvements are observed, symptoms often return after termination of treatment—sometimes to even worse levels. Nonetheless, since a "steroid response" may be an indication that immune-based therapies may be helpful.

Where symptoms lasting more than a year or very severe disease, intravenous immunoglobulin (IVIG) or plasmapheresis (i.e., plasma exchange to remove antibodies from the blood) may be helpful. A clinical study is currently being conducted using IVIG therapy with Gamunex®-C (Grifols Therapeutics), an intravenous immunoglobulin therapy (IVIG). In the worst cases, treatment with rituximab (Rituxan® from Genentech or MabThera® from Roche) may be suggested; rituximab is a chimeric monoclonal antibody against the protein CD20 normally used to treat non-Hodgkin's lymphoma). Such treatments are considered experimental for treatment of PANDAS/PANS and, thus are generally not covered by medical insurance. And such treatments can be very expensive—$50,000 or higher in some cases. Moreover, significant side effects—up to, and including, death—can result from such treatments.

The lack of clinical methods or tests to provide or confirm a PANS or PANDAS diagnosis presents significant obstacles to providing effective therapies to children suffering from PANS or PANDAS and their parents seeking such therapies. A physician, without such clinical methods or tests, may be less likely to conclude such a diagnosis simply based on the currently existing observational clinical criteria. After all, such current treatments regimes can be uncertain in outcome, expose the patient to significant side effects as well as long term, painful, and difficult procedures, and expose the parents to very high economic costs. Clinical methods and procedures to more accurately diagnose PANS or PANDAS will more easily allow physicians to arrive at such diagnosis with confidence and will, over time, allow treatments to move out of the experimental phase and to achieve insurance coverage.

Thus, there remains a need to provide such clinical methods and procedures. Indeed, this need has been unmet since the first identification of PANDAS/PANS in the 1980s and remains unmet today. The present invention provides such methods.

SUMMARY OF THE INVENTION

The present invention provides for a convenient and accurate diagnostic method for pediatric acute-onset neuropsychiatric syndrome (PANS) and pediatric autoimmune neuropsychiatric disorder associated with streptococci infection (PANDAS). The ability to reliably diagnose PANS and/or PANDAS using such a method allows treating clinicians to prescribe treatments in a more effective and timely manner than currently possible. Such ability to reliably diagnose PANS and PANDAS is expected to allow significant improvement in the outcomes for many patients with PANS and/or PANDAS.

Generally, the present diagnostic method can be applied to pediatric acute-onset neuropsychiatric syndrome (PANS) and similar diseases that may include autistic-like behaviors, anorexia nervosa, and deterioration in handwriting in addition to the typical contamination fears, obsessions and/or tics often associated with such conditions. Such similar diseases include pediatric autoimmune neuropsychiatric disorder associated with streptococci infection (PANDAS), rheumatic fever cases with Sydenham chorea, anorexia nervosa, autistic-like behaviors, obsessive compulsive disorder, Tourette's syndrome, Asperger's syndrome, and other related diseases with movement and neuropsychiatric symptoms. This present invention is especially adapted for the diagnosis of pediatric autoimmune neuropsychiatric disorder associated with streptococci infection (PANDAS) which is a subset of PANS. Unless otherwise specified, the term PANS is intended to include similar autoimmune-based diseases that may include autistic-like behaviors, anorexia nervosa, and deterioration in handwriting in addition to the typical contamination fears, obsessions and/or tics often associated with such conditions. The present invention is especially directed towards the diagnosis of PANDAS/PANS. The use of the present clinical diagnostic method avoids issues related to the many of conflicting names given to such conditions. If the present diagnostic method indicates the likelihood of such an underlying autoimmune disease presenting with neuropsychiatric symptoms, physicians can proceed more rapidly and with greater certainty to the determination of the appropriate treatment options (as discussed below).

The present invention comprises a panel of at least five clinical analyses or tests (using serum samples) to determine the risk of pediatric acute-onset neuropsychiatric syndrome (PANS) and/or pediatric autoimmune neuropsychiatric disorder associated with streptococcal infection (PANDAS) in an individual. Serum samples include, for example, blood serum and cerebrospinal fluid (CSF). Generally blood serum is preferred whereby whole blood is collected from the patient and the red blood cells are centrifuged down to separate it from the serum. The serum is removed can be assayed immediately or stored for later assay.

The first group of these clinical assays or tests include enzyme linked immunosorbent assays (ELISAs) to measure antibody titers against neuronal antigens present in the brain; these neuronal antigens include lysoganglioside, tubulin, dopamine receptor D1, dopamine receptor D2, human serotonin receptor 5HT2A, and human serotonin receptor 5HT2C. The present methods include at least four of these enzyme linked immunosorbent assays, preferably at least five of these enzyme linked immunosorbent assays, and more preferably all six of these enzyme linked immunosorbent assays. If only four assays are to be used from the first group, it is generally preferred that the neuronal antigens include lysoganglioside, tubulin, dopamine receptor D1, and dopamine receptor D2. The present methods also include a final assay to quantify calcium/calmodulin-dependent protein kinase activity using a neuronal cell line.

The present invention provides a method for determining the likelihood of a PANS or PANDAS diagnosis in a patient, said method comprising
(1) obtaining a serum sample from the patient;
(2) in a first assay, measuring a first antibody titer against lysoganglioside in a first portion of the serum sample and comparing the measured first antibody titer to a first normal control titer against lysoganglioside;
(3) in a second assay, measuring a second antibody titer against tubulin in a second portion of the serum sample and comparing the measured second antibody titer to a second normal control titer against tubulin;
(4) in a third assay, measuring a third antibody titer against dopamine receptor D1 in a third portion of the serum sample and comparing the measured third antibody titer to a third normal control titer against dopamine receptor D1;
(5) in a fourth assay, measuring a fourth antibody titer against dopamine receptor D2 in a fourth portion of the serum sample and comparing the measured fourth antibody titer to a fourth normal control titer against dopamine receptor D2; and
(6) in a final assay, measuring calcium/calmodulin-dependent protein kinase activity using a neuronal cell line in a separate portion of the serum sample and comparing the measured calcium/calmodulin-dependent protein kinase activity to a normal control calcium/calmodulin-dependent protein kinase activity;
whereby a PANS or PANDAS diagnosis is considered likely if any one of the first, second, third, or fourth antibody titers is significantly higher than the corresponding first, second, third, or fourth normal control titers, respectively; whereby the PANS or PANDAS diagnosis is considered highly likely if, independent of results from the first, second, third, and fourth assays, the measured calcium/calmodulin-dependent protein kinase activity is significantly higher than the normal control calcium/calmodulin-dependent protein kinase activity; and whereby the PANS or PANDAS diagnosis is considered not likely if (1) none of the first, second, third, or fourth antibody titers are significantly higher than the corresponding first, second, third, or fourth normal control titers, respectively, and (2) the measured calcium/calmodulin-dependent protein kinase activity is not significantly higher than the normal control calcium/calmodulin-dependent protein kinase activity.

The present invention also provides a method for treating PANS or PANDAS in a patient, said method comprising (A) requesting an analysis of a serum sample from a patient suspected of having PANS or PANDAS, wherein the analysis is capable of determining whether the patient is likely or highly likely to have PANS or PANDAS and (B), should the analysis determine that the patient is likely or highly likely to have PANS or PANDAS, administering antibiotic therapy, anti-inflammatory therapy, intravenous immunoglobulin therapy, plasmapheresis therapy, or combinations thereof to the patient;
wherein the analysis comprises the steps of:
(1) obtaining the serum sample from the patient;
(2) in a first assay, measuring a first antibody titer against lysoganglioside in a first portion of the serum sample and comparing the measured first antibody titer to a first normal control titer against lysoganglioside;
(3) in a second assay, measuring a second antibody titer against tubulin in a second portion of the serum sample and comparing the measured second antibody titer to a second normal control titer against tubulin;
(4) in a third assay, measuring a third antibody titer against dopamine receptor D1 in a third portion of the serum sample and comparing the measured third antibody titer to a third normal control titer against dopamine receptor D1;
(5) in a fourth assay, measuring a fourth antibody titer against dopamine receptor D2 in a fourth portion of the serum sample and comparing the measured fourth antibody titer to a fourth normal control titer against dopamine receptor D2; and
(6) in a final assay, measuring calcium/calmodulin-dependent protein kinase activity using a neuronal cell line in a separate portion of the serum sample and comparing the measured calcium/calmodulin-dependent protein kinase activity to a normal control calcium/calmodulin-dependent protein kinase activity;
whereby the patient is considered likely to have PANS or PANDAS if any one of the measured first, second, third, or fourth antibody titers is significantly higher than the corresponding first, second, third, or fourth normal control titers, respectively; whereby the patient is considered highly likely to have PANS or PANDAS if, independent of results from the first, second, third, and fourth assays, the measured calcium/calmodulin-dependent protein kinase activity is significantly higher than the normal control calcium/calmodulin-dependent protein kinase activity; and whereby the patient is considered not likely to have PANS or PANDAS if (1) none of the first, second, third, or fourth antibody titers are significantly higher than the corresponding first, second, third, or fourth normal control titers, respectively, and (2) the measured calcium/calmodulin-dependent protein kinase activity is not significantly higher than the normal control calcium/calmodulin-dependent protein kinase activity.

The present invention also provides a method for determining the likelihood of a PANS or PANDAS diagnosis in a patient, said method comprising
(1) obtaining a serum sample from the patient;
(2) carrying out at least four assays on the serum sample, wherein the at least four assays are selected from the group consisting of
(A) a first assay wherein a first antibody titer against lysoganglioside is measured in a first portion of the serum sample and then is compared to a first normal control titer against lysoganglio side,
(B) a second assay wherein a second antibody titer against tubulin is measured in a second portion of the serum sample and then is compared to a second normal control titer against tubulin,
(C) a third assay wherein a third antibody titer against dopamine receptor D1 is measured in a third portion of the serum sample and then is compared to a third normal control titer against dopamine receptor D1,
(D) a fourth assay wherein a fourth antibody titer against dopamine receptor D2 is measured in a fourth portion of the serum sample and then is compared to a fourth normal control titer against dopamine receptor D2,
(E) a fifth assay wherein a fifth antibody titer against human serotonin receptor 5HT2A is measured in a fifth portion of the serum sample and then is compared to a fifth normal control titer against human serotonin receptor 5HTT2A, and
(F) a sixth assay wherein a sixth antibody titer against human serotonin receptor 5HT2C is measured in a sixth portion of the serum sample and then is compared to a sixth normal control titer against human serotonin receptor 5HT2C; and
(3) carrying out a final assay wherein calcium/calmodulin-dependent protein kinase activity is measured using a neuronal cell line in a separate portion of the serum sample and then is compared to a normal control calcium/calmodulin-dependent protein kinase activity;

whereby a PANS or PANDAS diagnosis is considered likely if at least one of the measured first, second, third, fourth, fifth, or sixth antibody titers are significantly higher than the corresponding first, second, third, fourth, fifth, or sixth normal control titers, respectively; whereby the PANS or PANDAS diagnosis is considered highly likely if, independent of results from the first, second, third, fourth, fifth, or sixth assays, the measured calcium/calmodulin-dependent protein kinase activity is significantly higher than the normal control calcium/calmodulin-dependent protein kinase activity; and whereby the PANS or PANDAS diagnosis is considered not likely if (1) none of the measured first, second, third, fourth, fifth, or sixth antibody titers are significantly higher than the corresponding first, second, third, fourth, fifth, or sixth normal control titers, respectively, and (2) the measured calcium/calmodulin-dependent protein kinase activity is not significantly higher than the normal control calcium/calmodulin-dependent protein kinase activity. Preferably, step (2) involves carrying out at least five assays on the serum sample, wherein the at least five assays are selected from the group consisting of the first, second, third, fourth, fifth, and sixth assays. More preferable, step (2) involves carrying out all six assays on the serum sample from the group consisting of the first, second, third, fourth, fifth, and sixth assays.

The present invention also provides a method for treating PANS or PANDAS in a patient, said method comprising (A) requesting an analysis of a serum sample from a patient suspected of having PANS or PANDAS, wherein the analysis is capable of determining whether the patient is likely or highly likely to have PANS or PANDAS and (B), should the analysis determine that the patient is likely or highly likely to have PANS or PANDAS, administering antibiotic therapy, anti-inflammatory therapy, intravenous immunoglobulin therapy, plasmapheresis therapy, or combinations thereof to the patient;

wherein the analysis comprises the steps of:
(1) obtaining the serum sample from the patient;
(2) carrying out at least four assays on the serum sample, wherein the at least four assays are selected from the group consisting of
(A) a first assay wherein a first antibody titer against lysoganglioside is measured in a first portion of the serum sample and then is compared to a first normal control titer against lysoganglioside,
(B) a second assay wherein a second antibody titer against tubulin is measured in a second portion of the serum sample and then is compared to a second normal control titer against tubulin,
(C) a third assay wherein a third antibody titer against dopamine receptor D1 is measured in a third portion of the serum sample and then is compared to a third normal control titer against dopamine receptor D1,
(D) a fourth assay wherein a fourth antibody titer against dopamine receptor D2 is measured in a fourth portion of the serum sample and then is compared to a fourth normal control titer against dopamine receptor D2,
(E) a fifth assay wherein a fifth antibody titer against human serotonin receptor 5HT2A is measured in a fifth portion of the serum sample and then is compared to a fifth normal control titer against human serotonin receptor 5HTT2A, and
(F) a sixth assay wherein a sixth antibody titer against human serotonin receptor 5HT2C is measured in a sixth portion of the serum sample and then is compared to a sixth normal control titer against human serotonin receptor 5HT2C; and
(3) carrying out a final assay wherein calcium/calmodulin-dependent protein kinase activity is measured using a neuronal cell line in a separate portion of the serum sample and then is compared to a normal control calcium/calmodulin-dependent protein kinase activity;

whereby a PANS or PANDAS diagnosis is considered likely if at least one of the measured first, second, third, fourth, fifth, or sixth antibody titers are significantly higher than the corresponding first, second, third, fourth, fifth, or sixth normal control titers, respectively; whereby the PANS or PANDAS diagnosis is considered highly likely if, independent of results from the first, second, third, fourth, fifth, or sixth assays, the measured calcium/calmodulin-dependent protein kinase activity is significantly higher than the normal control calcium/calmodulin-dependent protein kinase activity; and whereby the PANS or PANDAS diagnosis is considered not likely if (1) none of the measured first, second, third, fourth, fifth, or sixth antibody titers are significantly higher than the corresponding first, second, third, fourth, fifth, or sixth normal control titers, respectively, and (2) the measured calcium/calmodulin-dependent protein kinase activity is not significantly higher than the normal control calcium/calmodulin-dependent protein kinase activity. Preferably, step (2) involves carrying out at least five assays on the serum sample, wherein the at least five assays are selected from the group consisting of the first, second, third, fourth, fifth, and sixth assays. More preferable, step (2) involves carrying out all six assays on the serum sample from the group consisting of the first, second, third, fourth, fifth, and sixth assays.

DETAILED DESCRIPTION OF THE PREFERRED EMBODIMENT

Figure 1:
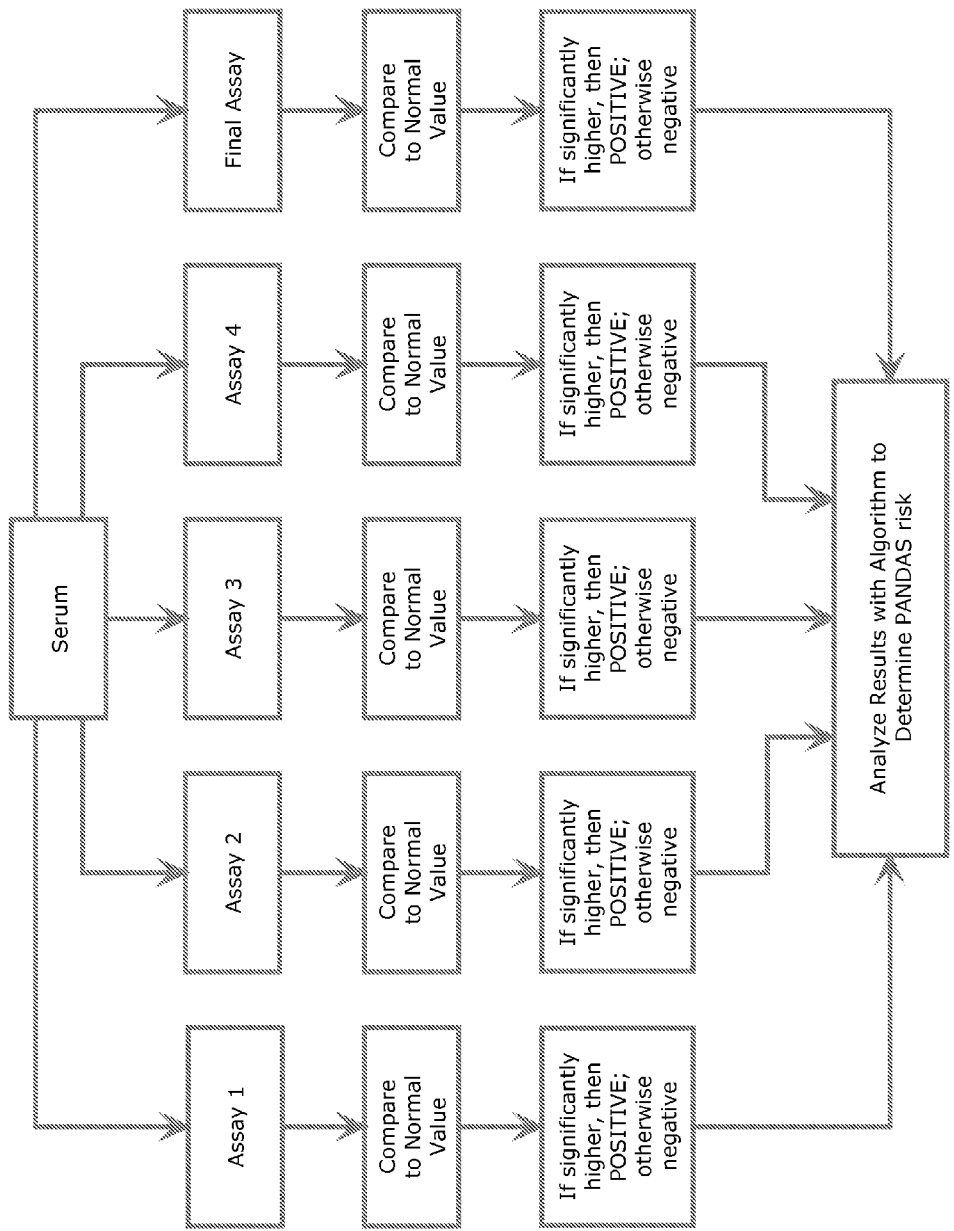
FIG. 1 provides a flowchart illustrating the method of the present invention using PANDAS as an illustrative example.

The present invention is a panel of at least five assays of patient sera for immune responses that may attack the brain/neurons and lead to the characteristic symptoms of pediatric acute-onset neuropsychiatric syndrome (PANS) and/or pediatric autoimmune neuropsychiatric disorder associated with streptococci infection (PANDAS. The testing provides a basis for diagnosis and treatment in the setting of symptoms consistent with PANS and/or PANDAS, including obsessions and compulsions, tics, autistic-like behaviors, anorexia nervosa, and deterioration in handwriting. The elevation above the normal mean or range of antibody titers in one or more of these assays indicates that the individual may be a candidate for treatment for PANS/PANDAS, including antibiotic therapy in the case of known infection, anti-inflammatory therapy, and also immunotherapy to treat the autoimmune/inflammatory condition in the brain. The present invention is especially adapted for providing a basis for diagnosis and treatment of pediatric autoimmune neuropsychiatric disorder associated with streptococci infection (PANDAS). Pediatricians are generally reluctant to recognize and treat PANS/PANDAS due to the lack of a reliable clinical test for the disease. Without such direct clinical evidence, many children will go undiagnosed and untreated. This invention provides such direct clinical evidence for PANS/PANDAS.

The present invention uses at least five tests or assays to diagnose the likelihood or risk of PANS/PANDAS in a specific child. These tests or assays include at least four assays selected from the group consisting of (1) a first enzyme linked immunosorbent assay (ELISA) to measure antibody titers against lysoganglioside in the patient's serum;

(2) a second enzyme linked immunosorbent assay to measure antibody titers against tubulin in the patient's serum;

(3) a third enzyme linked immunosorbent assay to measure antibody titers against dopamine receptor D1 in the patient's serum;

(4) a fourth enzyme linked immunosorbent assay to measure antibody titers against dopamine receptor D2 in the patient's serum;

(5) a fifth enzyme linked immunosorbent assay to measure antibody titers against human serotonin receptor 5HT2A in the patient's serum; and (6) a sixth enzyme linked immunosorbent assay to measure antibody titers against human serotonin receptor 5HT2C in the patient's serum. In addition to the at least four assays just mentioned, a final assay to quantify calcium/calmodulin-dependent protein kinase activity in a patient's serum using a neuronal cell line is used in all cases. The assays are described in some detail in the Examples below.

Other assays or modifications of these assays that measure the same parameters may be used so long as they provide the same predictive value. Such other assays will, of course, require additional collaboration efforts including establishing a baseline (i.e., normal controls) for comparison purposes. Thus, for example, the calcium/calmodulin-dependent protein kinase activity method described in Example 5 might, if confirmed by the appropriate testing procedures, be replaced by the similar, but non-radioactive, PepTag® Non-Radioactive Protein Kinase Assay offered by Promega.

Although only four of the enzyme linked immunosorbent assays described above (and the final assay to quantify calcium/calmodulin-dependent protein kinase activity) are required for the PANS/PANDAS diagnosis, the use of all six of the enzyme linked immunosorbent assays described above is generally preferred in order to confirm or strengthen the diagnosis that the individual may be a candidate for treatment for PANS/PANDAS. It is hoped that inclusion of all of these enzyme linked immunosorbent assays described above will allow treatments for PANS/PANDAS to more quickly move out of the current experimental phase and to achieve insurance coverage by increasing the accuracy of the PANS/PANDAS diagnosis.

The presence of significantly elevated antibodies and those that signal neuronal cells indicate autoimmune disease. Even if the antibodies are later proven not to be the cause of PANS/PANDAS, they appear to at least represent "smoke that indicates fire somewhere in the body"; thus, they act as markers for PANS/PANDAS in the present methods. Although not wishing to be bound by theory, it is currently believed, however, that they probably do play a causal role in the disease due to their activation of neurons.

FIG. 1 generally illustrates the general procedure used in the present invention employing the enzyme linked immunosorbent Assays 1 through 4 and the calcium/calmodulin-dependent protein kinase activity method (Final Assay). Serum derived from patient blood is analyzed in using the procedures described in the Examples. In the case of each analysis, the measured amounts from the assays are compared to normal controls; the normal control values are obtained from non-PANS/PANDAS subjects of similar ages using the same assays. For a given assay, if the measured amounts from the assays are significantly higher than that of the normal controls, those assays are considered positive; otherwise, they are considered negative. The results of the five assays are then analyzed using an algorithm to determine the subject's risk or likelihood for PANS/PANDAS. Should enzyme linked immunosorbent Assays 6 and 7 also be used (either as replacement for two of the assays or in combination with Assays 1 through 4), they would be evaluated and used in the present methods in a similar manner.

For purposes of this invention, "highly significant" with regard to the enzyme linked immunosorbent assays (Assays 1 through 6) is intended to mean that the measure amount is at least 1.5 times, and preferably at least 2 times, the standard deviation greater than the mean value of the normal control for each assay. For purposes of this invention, "highly significant" with regard to the Final Assay (i.e., CaM Kinase assay) is intended to mean that the measure amount is at least 2 times, and preferably at least 3 times, the standard deviation greater than the mean value of the normal control for each assay. Thus, for example, the measure value of any of Assays 1 through 6 must be at least 1.5 (and preferably at least 2) standard deviations of the corresponding normal control greater than the mean of the corresponding normal control to be considered highly significant; and the measured value of Final Assay must be at least 2 (and preferably at least 3) standard deviations of the corresponding normal control greater than the mean of the corresponding normal control to be considered highly significant. The normal control data (including the mean and the standard deviation) for each of the assays (based on blood serum) is given in Example 8. Of course, these values may shift slightly as, and if, further data on normal (non-PANS/PANDAS) controls is added to the database. Of course, care must be taken exclude patients in the normal control group that are even suspected of having PANS/PANDAS.

Figure 2:
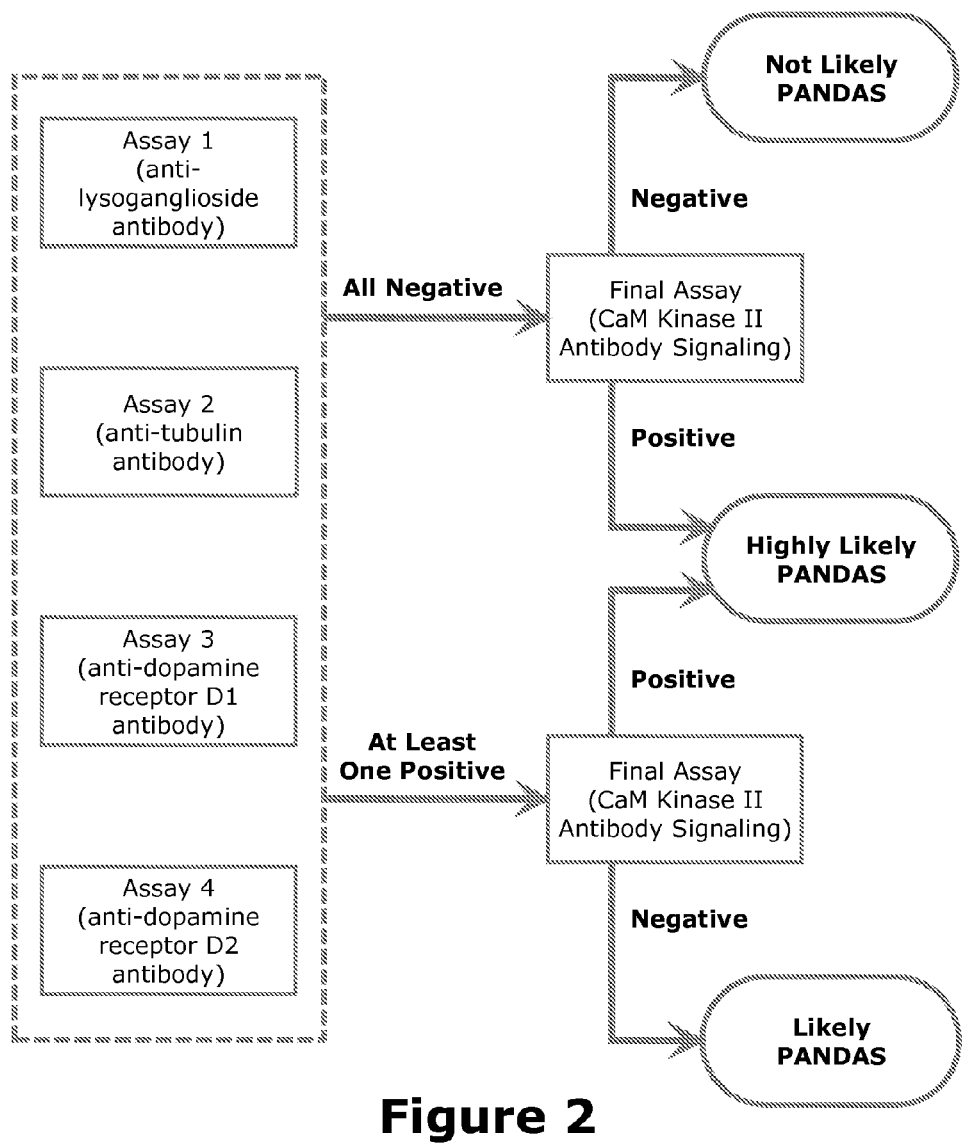
FIG. 2 provides a flowchart illustrating the general algorithm used in the present invention using PANDAS as an illustrative example.

FIG. 2 illustrates one algorithm used to evaluate the results of the present invention. In this illustrate case, only Assays 1 through 4 and the Final Assay are used. If Assays 1 through 4 are negative and if the Final Assay is negative, then it is not likely that the patient has PANS/PANDAS. But if the Final Assay is positive for functional signaling antibody, then it is HIGHLY LIKELY that the patient has PANS/PANDAS since this assay is responsive to antibodies which are elevated at PANS/PANDAS exacerbations; for purposes of this invention, HIGHLY LIKELY indicates that the probability of PANS/PANDAS is greater than about 60 percent. If at least one of Assays 1 to 4 is positive and if the Final Assay 5 is negative, then it is LIKELY that the patient has PANS/PANDAS; for purposes of this invention, LIKELY indicates that the probability of PANS/PANDAS is between about 40 to about 60 percent. In other words, if the Final Assay is positive (independent of the results of Assays 1 through 4) then it is HIGHLY LIKELY that the patient has PANS/PANDAS. If the Final Assay is negative and at least one of Assays 1 through 4 is positive, then it is LIKELY that the patient has PANS/PANDAS. If all assays are negative, then it is not likely that the patient has PANS/PANDAS. Nonetheless for cases where all assays are negative, and especially if symptoms persist, the tests should be repeated at a later time (say a month later) to confirm the original test.

If the Assays 5 and 6 are employed (either in combination with the Assays 1 through 4 or to replace one or more of Assays 1 through 4), similar algorithms would be used. If Assays 1 through 6 are used, then a positive result for the Final Assay (independent of the results of Assays 1 through 6) would still indicate that it is HIGHLY LIKELY that the patient has PANS/PANDAS. If at least one of Assays 1 through 6 is positive and if the Final Assay is negative, then it is LIKELY that the patient has PANS/PANDAS. In the event that Final Assay is positive and one or more Assays 1 through 6 are positive, then it is HIGHLY LIKELY that the patient has PANS/PANDAS; this likelihood should effectively increase as the number of positive results for Assays 1 through 6 increases.

If desired, the algorithm could be modified to include other parameters. Thus, for example, an additional parameter might be the observation of one or more of the observational clinical criteria used in the current PANS/PANDAS diagnostic procedure or the presence of streptococcal infection. Thus, the observance of such observational clinical criteria could be used to increase the likelihood of a PANS/PANDAS diagnosis as presented in FIG. 2. Moreover, the algorithm might be modified to indicate increase likelihood of PANS/PANDAS if two or more of Assays 1 through 6 were found to be positive. Also if desired, the algorithm could be modified by applying a numerical score to each of the assays (say on a scale of 1 to 10) and then summing the results of the five or more assays to obtain an overall score. The additional of the secondary assays could be used to increase even further the accuracy of the present methods. Thus, should one or more of Assays 1 through 4 and Final Assay are positive, a positive result for one or more of Assays 5 and 6, if included, would further strengthen the diagnosis of PANS/PANDAS.

As further data is developed (e.g., as data from additional PANS/PANDAS patients evaluated by the present method), such data should be added to the database. Additional consideration of the database—especially as it expands— may lead to further modification of the appropriate algorithm and/or additional criteria or tests to be included in the method.

Figure 3:
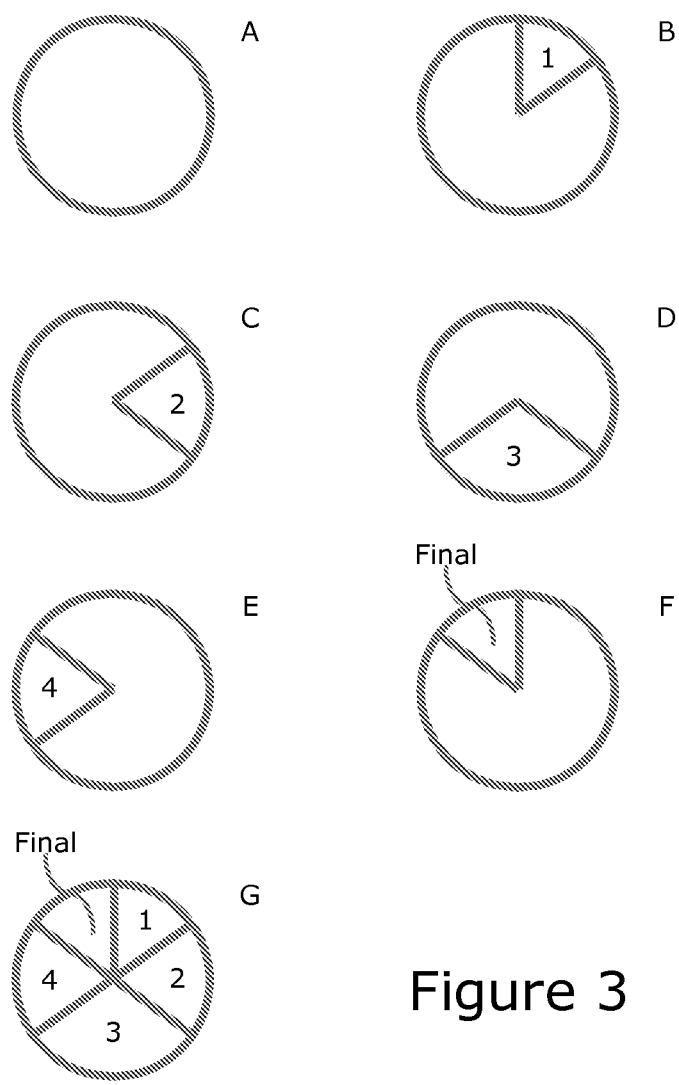
FIG. 3 provides a schematic (but theoretic) illustration of the necessity at least five assays of the present invention to provide a PANDAS diagnosis.

FIG. 3 provides a schematic (but theoretical) illustration of the necessity of multiple assays of the present invention to provide a PANS/PANDAS diagnosis. Only Assays 1 through 4 and the Final Assay are used in this illustrative example. Assume that the circle in Panel A represents a given population of patients having PANS/PANDAS. Further assume that Panels B though E represent the portions of the population that test positive in Assays 1 through 4, respectively, and that Panel F represents the portion of the population that test positive in the Final Assay. All of the patients in the population should test positive for at least one of the assays; some may test positive for more than one of the assays. But only by performing all five assays can all patients in the population be identified with PANS/PANDAS as shown in Panel G. Based on the data generated to date, it appears that about 90 to 95 percent of a given population having PANS/PANDAS would be identified by the present method. The addition of assays not shown in the figure (e.g., Assays 5 and 6) may further increase the likelihood of accurately identifying PANS or PANDAS. In cases where the patient has been previously treated with steroids, IVIG or plasma exchange (generally within about one to two months prior to testing), false negative results are possible. The possibility of such previous treatments should be taken into account in appropriate cases when evaluating the results. Thus, follow up evaluations using the assays of this invention should be considered when such prior treatments have been carried out to reduce the risk of such false negative results.

All references and publications cited herein, including references and publications included in the Appendix, are hereby incorporated by reference in their entirety.

The following Examples 1 through 6 provide protocols for Assays 1 through 6, respectively; Example 7 provides a protocol for the Final Assay of this method.

Example 1

Anti-Lysoganglioside Antibody Titer Protocol

The first assay is used to measure human serum IgG titers against lysoganglioside using the below described ELISA method. The antibodies are detected by coating microtiter plate wells with specific antigens, incubating the plates with serial dilutions of human sera, and washing away unbound antibodies. A secondary antibody conjugated to alkaline phosphatase is added to the plate and, after incubation, the excess conjugate is washed away. A color-developing substrate solution is then added. The amount of color developed is directly proportional to the amount of antibody in the sample. As always, when working with human fluids, biosafety practices must be followed.

The following materials were used:

| Material | Details |
| --- | --- |
| Lysoganglioside GM1 | from bovine brain (Sigma-Aldrich - G5660); store at −20° C. |
| 96-Well ELISA plates | Immulon IV flat bottom plates (Thermo Scientific) |
| Multichannel pipet | Fisherbrand |
| Plastic wrap | |
| Single channel pipetters | Gibson |
| Disposable tips | VWR |
| Disposable serological pipets | Falcon |
| Microcentrifuge disposable tubes | Fisherbrand |
| Plastic squirt bottles | |
| Refrigerated microcentrifuge | International Equipment Company |
| Microtiter plate reader | spectrophotometer with 405 nm filter-based optical module (BioTek) |
| DI water | |

| Material | Details |
| --- | --- |
| Wash Buffer | PBS (8.0 g NaCl, 0.2 g $KH_2PO_4$, 1.08 g $Na_2HPO_4$, 0.2 g KCl, and 0.1 g $NaN_3$ in 1000 ml DI water) + 0.05% Tween 20 (Sigma P7949); store at room temperature |
| Block and diluent buffer | 1% Bovine Serum Albumin (Fisher) in PBS, store at 4° C. |
| Carbonate-bicarbonate coating buffer | 1.59 g $Na_2CO_3$, 2.93 g $NaHCO_3$, and 0.2 g $NaN_3$ in 500 ml DI water, pH to 9.6, store at 4° C. in amber bottle |
| Diethanolamine developing buffer | 97 ml diethanolamine, 800 ml DI $H_2O$, 0.2 g $NaN_3$, 100 mg $MgCl_2 \times 6H_2O$, DI $H_2O$ to final volume of 1000 ml, pH to 9.8, store at 4° C. in amber bottle |
| Secondary antibodies | Anti-human IgG (γ-chain specific), F(ab')2fragment - Alkaline Phosphatase, produced in goat, affinity isolated antibody (Sigma A3312) |
| Substrate solution | p-Nitrophenyl phosphate solution - 1 mg Sigma S0942 per 1 ml diethanolamine developing buffer |

The following procedure was used:

1. Reconstitute lysoganglioside-GM1 (lyophilized powder) in PBS (no tween) to 1 mg/ml. Dilute lysoganglioside to 20 μg/ml in carbonate/bicarbonate coating buffer. Using a multichannel pipet, dispense 50 μl of the antigen solution into each well. Tap the plate gently to make sure the antigen solution is evenly distributed in the wells.
2. Wrap coated plates in plastic wrap and incubate overnight at 4° C. These plates can be stored wrapped in plastic at 4° C. for up to 2 weeks.
3. Using a plastic squirt bottle wash plates by filling all wells five times with PBS/0.05% Tween (wash buffer). Gently tap plates over tissue paper to remove residual wash buffer.
4. Using a multichannel pipet, block the plates by dispensing 100 μl of 1% BSA into all wells. Wrap blocked plates in plastic wrap and incubate for an hour at 37° C.
5. Centrifuge serum samples at 4° C., 10,000 rpm for 10 minutes. Prepare sera dilutions. Initial sera dilution is 1:10 in 1% BSA in PBS. Further 1:2 dilutions in 1% BSA in PBS are made with a final dilution of 1:1280 (or higher if necessary). Four serum samples as well as a positive and negative control, all in duplicates, are run per plate.
6. Wash plate as described in step 3 above).
7. Place 50 μl of diluted serum sample on plate on duplicate wells and 50 μl of 1% BSA on two blank wells. The average OD value obtained from the blank wells will be deducted from the rest of the wells as background. Wrap coated plates in plastic wrap and incubate overnight at 4° C.
8. Wash plate as described in step 3 above.
9. Secondary antibody is diluted 1:500 in 1% BSA. Using a multichannel pipet add 50 μl of the diluted conjugate to all wells, wrap plate, and incubate for one hour at 37° C.
10. Wash plate as described in step 3 above.
11. Using a multichannel pipet add the substrate solution (50 μl per well). Place on the plate and incubate at room temperature for 120 minutes.
12. Read optical density (OD) at 405 nm immediately after 120 minute incubation.
13. The antibody titer is calculated as the lowest serum dilution reading an OD of 0.10 after 120 minute incubation.

Example 2

Anti-Tubulin Antibody Titer Protocol

The second assay is used to measure human serum IgG titers against tubulin using the below described ELISA method. The antibodies are detected by coating microtiter plate wells with specific antigens, incubating the plates with serial dilutions of human sera, and washing away unbound antibodies. A secondary antibody conjugated to alkaline phosphatase is added to the plate and, after incubation, the excess conjugate is washed away. A color-developing substrate solution is then added. The amount of color developed is directly proportional to the amount of antibody in the sample. As always, when working with human fluids, biosafety practices must be followed.

The following materials were used:

| Material | Details |
| --- | --- |
| Tubulin | from bovine brain (MP Biomedicals - 08771121); store lyophilized powder at 4° C., once reconstituted with included PIPES buffer store at −80° C. |
| 96-Well ELISA plates | Immulon IV flat bottom plates (Thermo Scientific) |
| Multichannel pipet | Fisherbrand |
| Plastic wrap | |
| Single channel pipetters | Gibson |
| Disposable tips | VWR |
| Disposable serological pipets | Falcon |
| Microcentrifuge disposable tubes | Fisherbrand |
| ELISA plate washer | BioTek |
| Refrigerated microcentrifuge | International Equipment Company |
| Microtiter plate reader | spectrophotometer with 405 nm filter-based optical module (BioTek) |
| DI water | |

-continued

| Material | Details |
|---|---|
| Wash Buffer | PBS (8.0 g NaCl, 0.2 g $KH_2PO_4$, 1.08 g $Na_2HPO_4$, 0.2 g KCl, and 0.1 g $NaN_3$ in 1000 ml DI water) + 0.05% Tween 20 (Sigma P7949); store at room temperature |
| Block and diluent buffer | 1% Bovine Serum Albumin (Fisher) in PBS, store at 4° C. |
| Carbonate-bicarbonate coating buffer | 1.59 g $Na_2CO_3$, 2.93 g $NaHCO_3$, and 0.2 g $NaN_3$ in 500 ml DI water, pH to 9.6, store at 4° C. in amber bottle |
| Diethanolamine developing buffer | 97 ml diethanolamine, 800 ml DI $H_2O$, 0.2 g $NaN_3$, 100 mg $MgCl_2 \times 6H_2O$, DI $H_2O$ to final volume of 1000 ml, pH to 9.8, store at 4° C. in amber bottle |
| Secondary antibodies | Anti-human IgG (γ-chain specific), F(ab')2fragment - Alkaline Phosphatase, produced in goat, affinity isolated antibody (Sigma A3312) |
| Substrate solution | p-Nitrophenyl phosphate solution - 1 mg Sigma S0942 per 1 ml diethanolamine developing buffer |

The following procedure was used:

1. Reconstitute tubulin (lyophilized powder) in included PIPES buffer to 5 mg/ml. (If not used immediately, divide into appropriate aliquots and store at −80° C.) Dilute tubulin to 10 µg/ml in carbonate/bicarbonate coating buffer. Using a multichannel pipet, dispense 50 µl of the antigen solution into each well. Tap the plate gently to make sure the antigen solution is evenly distributed in the wells.

2. Wrap coated plates in plastic wrap and incubate overnight at 4° C. These plates can be stored wrapped in plastic at 4° C. for up to 2 weeks.

3. Using an ELISA plate washer, wash plates by filling all wells five times with PBS/0.05% Tween (wash buffer). Gently tap plates over tissue paper to remove residual wash buffer.

4. Using a multichannel pipet, block the plates by dispensing 100 µl of 1% BSA into all wells. Wrap blocked plates in plastic wrap and incubate for an hour at 37° C.

5. Centrifuge serum samples at 4° C., 10,000 rpm for 10 minutes. Prepare sera dilutions. Initial sera dilution is 1:10 in 1% BSA in PBS. Further 1:2 dilutions in 1% BSA in PBS are made with a final dilution of 1:32000 (or higher if necessary). Four serum samples as well as a positive and negative control, all in duplicates, are run per plate.

6. Wash plate as described in step 3 above).

7. Place 50 µl of diluted serum sample on plate on duplicate wells and 50 µl of 1% BSA on two blank wells. The average OD value obtained from the blank wells will be deducted from the rest of the wells as background. Wrap coated plates in plastic wrap and incubate overnight at 4° C.

8. Wash plate as described in step 3 above.

9. Secondary antibody is diluted 1:500 in 1% BSA. Using a multichannel pipet add 50 µl of the diluted conjugate to all wells, wrap plate, and incubate for one hour at 37° C.

10. Wash plate as described in step 3 above.

11. Using a multichannel pipet add the substrate solution (50 µl per well). Place on the plate and incubate at room temperature for 120 minutes.

12. Read optical density (OD) at 405 nm immediately after 120 minute incubation.

13. The antibody titer is calculated as the lowest serum dilution reading an OD of 0.10 after 120 minute incubation.

Example 3

Anti-Dopamine D1 Receptor Antibody Titer Protocol

The third assay is used to measure human serum IgG titers against dopamine D1 receptors using the below described ELISA method. The antibodies are detected by coating microtiter plate wells with specific antigens, incubating the plates with serial dilutions of human sera, and washing away unbound antibodies. A secondary antibody conjugated to alkaline phosphatase is added to the plate and, after incubation, the excess conjugate is washed away. A color-developing substrate solution is then added. The amount of color developed is directly proportional to the amount of antibody in the sample. As always, when working with human fluids, biosafety practices must be followed.

The following materials were used:

| Material | Details |
|---|---|
| Dopamine D1 receptor | 400 µl frozen aliquot, membranes from cells (Membrane Target Systems, Perkin Elmer 6110513400UA); at −80° C. |
| 96-Well ELISA plates | Immulon IV flat bottom plates (Thermo Scientific) |
| Plastic wrap | |
| Multichannel pipet | Fisherbrand |
| Single channel pipetters | Gibson |
| Disposable tips | VWR |
| Disposable serological pipets | Falcon |
| Microcentrifuge disposable tubes | Fisherbrand |
| ELISA plate washer | BioTek |
| Refrigerated microcentrifuge | International Equipment Company |
| Microtiter plate reader | spectrophotometer with 405 nm filter-based optical module (BioTek) |
| DI water | |

-continued

| Material | Details |
|---|---|
| Wash Buffer | PBS (8.0 g NaCl, 0.2 g $KH_2PO_4$, 1.08 g $Na_2HPO_4$, 0.2 g KCl, and 0.1 g $NaN_3$ in 1000 ml DI water) + 0.05% Tween 20 (Sigma P7949); store at room temperature |
| Block and diluent buffer | 1% Bovine Serum Albumin (Fisher) in PBS, store at 4° C. |
| Carbonate-bicarbonate coating buffer | 1.59 g $Na_2CO_3$, 2.93 g $NaHCO_3$, and 0.2 g $NaN_3$ in 500 ml DI water, pH to 9.6, store at 4° C. in amber bottle |
| Diethanolamine developing buffer | 97 ml diethanolamine, 800 ml DI $H_2O$, 0.2 g $NaN_3$, 100 mg $MgCl_2 \times 6H_2O$, DI $H_2O$ to final volume of 1000 ml, pH to 9.8, store at 4° C. in amber bottle |
| Secondary antibodies | Anti-human IgG (γ-chain specific), F(ab')2fragment - Alkaline Phosphatase, produced in goat, affinity isolated antibody (Sigma A3312) |
| Substrate solution | p-Nitrophenyl phosphate solution - 1 mg Sigma S0942 per 1 ml diethanolamine developing buffer |

The following procedure was used:

1. Dilute dopamine D1 receptor to 10 μg/ml in carbonate/bicarbonate coating buffer. Using a multichannel pipet, dispense 50 μl of the antigen solution into each well. Tap the plate gently to make sure the antigen solution is evenly distributed in the wells.

2. Wrap coated plates in plastic wrap and incubate overnight at 4° C. These plates can be stored wrapped in plastic at 4° C. for up to 2 weeks.

3. Using an ELISA plate washer, wash plates by filling all wells five times with PBS/0.05% Tween (wash buffer). Gently tap plates over tissue paper to remove residual wash buffer.

4. Using a multichannel pipet, block the plates by dispensing 100 μl of 1% BSA into all wells. Wrap blocked plates in plastic wrap and incubate for an hour at 37° C.

5. Centrifuge serum samples at 4° C., 10,000 rpm for 10 minutes. Prepare sera dilutions. Initial sera dilution is 1:10 in 1% BSA in PBS. Further 1:2 dilutions in 1% BSA in PBS are made with a final dilution of 1:32000 (or higher if necessary). Four serum samples as well as a positive and negative control, all in duplicates, are run per plate.

6. Wash plate as described in step 3 above.

7. Place 50 μl of diluted serum sample on plate on duplicate wells and 50 μl of 1% BSA on two blank wells. The average OD value obtained from the blank wells will be deducted from the rest of the wells as background. Wrap coated plates in plastic wrap and incubate overnight at 4° C.

8. Wash plate as described in step 3 above.

9. Secondary antibody is diluted 1:1000 in 1% BSA. Using a multichannel pipet add 50 μl of the diluted conjugate to all wells, wrap plate, and incubate for one hour at 37° C.

10. Wash plate as described in step 3 above.

11. Using a multichannel pipet add the substrate solution (50 μl per well). Place on the plate and incubate at room temperature for 120 minutes.

12. Read optical density (OD) at 405 nm immediately after 120 minute incubation.

13. The antibody titer is calculated as the lowest serum dilution reading an OD of 0.10 after 120 minute incubation.

Example 4

Anti-Dopamine D2 Antibody Receptor Titer Protocol

The fourth assay involves the measurement of human serum IgG titers against dopamine D2 receptors by ELISA. The antibodies are detected by coating microtiter plate wells with specific antigens, incubating the plates with serial dilutions of human sera, and washing away unbound antibodies. A secondary antibody conjugated to alkaline phosphatase is added to the plate and, after incubation, the excess conjugate is washed away. A color-developing substrate solution is then added. The amount of color developed is directly proportional to the amount of antibody in the sample. As always, when working with human fluids, biosafety practices must be followed.

The following materials were used:

| Material | Details |
|---|---|
| Dopamine D2 receptor | 400 μl frozen aliquot, membranes from cells (Membrane Target Systems, Perkin Elmer 6110137400UA); store at −80° C. |
| 96-Well ELISA plates | Immulon IV flat bottom plates (Thermo Scientific) |
| Plastic wrap | |
| Multichannel pipet | Fisherbrand |
| Single channel pipetters | Gibson |
| Disposable tips | VWR |
| Disposable serological pipets | Falcon |
| Microcentrifuge disposable tubes | Fisherbrand |
| ELISA plate washer | BioTek |
| Refrigerated microcentrifuge | International Equipment Company |
| Microtiter plate reader | spectrophotometer with 405 nm filter-based optical module (BioTek) |
| DI water | |
| Wash Buffer | PBS (8.0 g NaCl, 0.2 g $KH_2PO_4$, 1.08 g $Na_2HPO_4$, 0.2 g KCl, and 0.1 g $NaN_3$ in 1000 ml DI water) + 0.05% Tween 20 (Sigma P7949); store at room temperature |

| Material | Details |
| --- | --- |
| Block and diluent buffer | 1% Bovine Serum Albumin (Fisher) in PBS, store at 4° C. |
| Carbonate-bicarbonate coating buffer | 1.59 g $Na_2CO_3$, 2.93 g $NaHCO_3$, and 0.2 g $NaN_3$ in 500 ml DI water, pH to 9.6, store at 4° C. in amber bottle |
| Diethanolamine developing buffer | 97 ml diethanolamine, 800 ml DI $H_2O$, 0.2 g $NaN_3$, 100 mg $MgCl_2 \times 6H_2O$, DI $H_2O$ to final volume of 1000 ml, pH to 9.8, store at 4° C. in amber bottle |
| Secondary antibodies | Anti-human IgG (γ-chain specific), F(ab')2 fragment - Alkaline Phosphatase, produced in goat, affinity isolated antibody (Sigma A3312) |
| Substrate solution | p-Nitrophenyl phosphate solution - 1 mg Sigma S0942 per 1 ml diethanolamine developing buffer |

The following procedure was used:

1. Dilute dopamine D2 receptor to 10 µg/ml in carbonate/bicarbonate coating buffer. Using a multichannel pipet, dispense 50 µl of the antigen solution into each well. Tap the plate gently to make sure the antigen solution is evenly distributed in the wells.

2. Wrap coated plates in plastic wrap and incubate overnight at 4° C. These plates can be stored wrapped in plastic at 4° C. for up to 2 weeks.

3. Using an ELISA plate washer, wash plates by filling all wells five times with PBS/0.05% Tween (wash buffer). Gently tap plates over tissue paper to remove residual wash buffer.

4. Using a multichannel pipet, block the plates by dispensing 100 µl of 1% BSA into all wells. Wrap blocked plates in plastic wrap and incubate for an hour at 37° C.

5. Centrifuge serum samples at 4° C., 10,000 rpm for 10 minutes. Prepare sera dilutions. Initial sera dilution is 1:10 in 1% BSA in PBS. Further 1:2 dilutions in 1% BSA in PBS are made with a final dilution of 1:32000 (or higher if necessary). Four serum samples as well as a positive and negative control, all in duplicates, are run per plate.

6. Wash plate as described in step 3 above.

7. Place 50 µl of diluted serum sample on plate on duplicate wells and 50 µl of 1% BSA on two blank wells. The average OD value obtained from the blank wells will be deducted from the rest of the wells as background. Wrap coated plates in plastic wrap and incubate overnight at 4° C.

8. Wash plate as described in step 3 above.

9. Secondary antibody is diluted 1:1000 in 1% BSA. Using a multichannel pipet add 50 µl of the diluted conjugate to all wells, wrap plate, and incubate for one hour at 37° C.

10. Wash plate as described in step 3 above.

11. Using a multichannel pipet add the substrate solution (50 µl per well). Place on the plate and incubate at room temperature for 120 minutes.

12. Read optical density (OD) at 405 nm immediately after 120 minute incubation.

13. The antibody titer is calculated as the lowest serum dilution reading an OD of 0.10 after 120 minute incubation.

Example 5

Anti-Serotonin 5HT2A Antibody Receptor Titer Protocol

The fifth assay involves the measurement of human serum IgG titers against serotonin 5HT2A receptors by ELISA. The antibodies are detected by coating microtiter plate wells with specific antigens, incubating the plates with serial dilutions of human sera, and washing away unbound antibodies. A secondary antibody conjugated to alkaline phosphatase is added to the plate and, after incubation, the excess conjugate is washed away. A color-developing substrate solution is then added. The amount of color developed is directly proportional to the amount of antibody in the sample. As always, when working with human fluids, biosafety practices must be followed.

The following materials were used:

| Material | Details |
| --- | --- |
| Serotonin 5HT2A receptor | 400 µl frozen aliquot, membranes from cells (Membrane Target Systems, Perkin Elmer ES-313-M400UA); store at −80° C. |
| 96-Well ELISA plates | Immulon IV flat bottom plates (Thermo Scientific) |
| Plastic wrap | |
| Multichannel pipet | Fisherbrand |
| Single channel pipetters | Gibson |
| Disposable tips | VWR |
| Disposable serological pipets | Falcon |
| Microcentrifuge disposable tubes | Fisherbrand |
| ELISA plate washer | BioTek |
| Refrigerated microcentrifuge | International Equipment Company |
| Microtiter plate reader | spectrophotometer with 405 nm filter-based optical module (BioTek) |
| DI water | |
| Wash Buffer | PBS (8.0 g NaCl, 0.2 g $KH_2PO_4$, 1.08 g $Na_2HPO_4$, 0.2 g KCl, and 0.1 g $NaN_3$ in 1000 ml DI water) + 0.05% Tween 20 (Sigma P7949); store at room temperature |
| Block and diluent buffer | 1% Bovine Serum Albumin (Fisher) in PBS, store at 4° C. |
| Carbonate-bicarbonate coating buffer | 1.59 g $Na_2CO_3$, 2.93 g $NaHCO_3$, and 0.2 g $NaN_3$ in 500 ml DI water, pH to 9.6, store at 4° C. in amber bottle |

-continued

| Material | Details |
|---|---|
| Diethanolamine developing buffer | 97 ml diethanolamine, 800 ml DI H$_2$0, 0.2 g NaN$_3$, 100 mg MgCl$_2$ × 6H$_2$O, DI H$_2$0 to final volume of 1000 ml, pH to 9.8, store at 4° C. in amber bottle |
| Secondary antibodies | Anti-human IgG (γ-chain specific), F(ab')2fragment - Alkaline Phosphatase, produced in goat, affinity isolated antibody (Sigma A3312) |
| Substrate solution | p-Nitrophenyl phosphate solution - 1 mg Sigma S0942 per 1 ml diethanolamine developing buffer |

The following procedure was used:

1. Dilute serotonin 5HT2A receptor to 10 µg/ml in carbonate/bicarbonate coating buffer. Using a multichannel pipet, dispense 50 µl of the antigen solution into each well. Tap the plate gently to make sure the antigen solution is evenly distributed in the wells.

2. Wrap coated plates in plastic wrap and incubate overnight at 4° C. These plates can be stored wrapped in plastic at 4° C. for up to 2 weeks.

3. Using an ELISA plate washer, wash plates by filling all wells five times with PBS/0.05% Tween (wash buffer). Gently tap plates over tissue paper to remove residual wash buffer.

4. Using a multichannel pipet, block the plates by dispensing 100 µl of 1% BSA into all wells. Wrap blocked plates in plastic wrap and incubate for an hour at 37° C.

5. Centrifuge serum samples at 4° C., 10,000 rpm for 10 minutes. Prepare sera dilutions. Initial sera dilution is 1:10 in 1% BSA in PBS. Further 1:2 dilutions in 1% BSA in PBS are made with a final dilution of 1:32000 (or higher if necessary). Four serum samples as well as a positive and negative control, all in duplicates, are run per plate.

6. Wash plate as described in step 3 above.

7. Place 50 µl of diluted serum sample on plate on duplicate wells and 50 µl of 1% BSA on two blank wells. The average OD value obtained from the blank wells will be deducted from the rest of the wells as background. Wrap coated plates in plastic wrap and incubate overnight at 4° C.

8. Wash plate as described in step 3 above.

9. Secondary antibody is diluted 1:1000 in 1% BSA. Using a multichannel pipet add 50 µl of the diluted conjugate to all wells, wrap plate, and incubate for one hour at 37° C.

10. Wash plate as described in step 3 above.

11. Using a multichannel pipet add the substrate solution (50 µl per well). Place on the plate and incubate at room temperature for 120 minutes.

12. Read optical density (OD) at 405 nm immediately after 120 minute incubation.

13. The antibody titer is calculated as the lowest serum dilution reading an OD of 0.10 after 120 minute incubation.

Example 6

Anti-Serotonin 5HT2C Antibody Receptor Titer Protocol

The sixth assay involves the measurement of human serum IgG titers against serotonin 5HT2CA receptors by ELISA. The antibodies are detected by coating microtiter plate wells with specific antigens, incubating the plates with serial dilutions of human sera, and washing away unbound antibodies. A secondary antibody conjugated to alkaline phosphatase is added to the plate and, after incubation, the excess conjugate is washed away. A color-developing substrate solution is then added. The amount of color developed is directly proportional to the amount of antibody in the sample. As always, when working with human fluids, biosafety practices must be followed.

The following materials were used:

| Material | Details |
|---|---|
| Serotonin 5HT2C receptor | 400 µl frozen aliquot, membranes from cells (Membrane Target Systems, Perkin Elmer ES-315-M400UA); store at −80° C. |
| 96-Well ELISA plates | Immulon IV flat bottom plates (Thermo Scientific) |
| Plastic wrap | |
| Multichannel pipet | Fisherbrand |
| Single channel pipetters | Gibson |
| Disposable tips | VWR |
| Disposable serological pipets | Falcon |
| Microcentrifuge disposable tubes | Fisherbrand |
| ELISA plate washer | BioTek |
| Refrigerated microcentrifuge | International Equipment Company |
| Microtiter plate reader | spectrophotometer with 405 nm filter-based optical module (BioTek) |
| DI water | |
| Wash Buffer | PBS (8.0 g NaCl, 0.2 g KH$_2$PO$_4$, 1.08 g Na$_2$HPO$_4$, 0.2 g KCl, and 0.1 g NaN$_3$ in 1000 ml DI water) + 0.05% Tween 20 (Sigma P7949); store at room temperature |
| Block and diluent buffer | 1% Bovine Serum Albumin (Fisher) in PBS, store at 4° C. |
| Carbonate-bicarbonate coating buffer | 1.59 g Na$_2$CO$_3$, 2.93 g NaHCO$_3$, and 0.2 g NaN$_3$ in 500 ml DI water, pH to 9.6, store at 4° C. in amber bottle |
| Diethanolamine developing buffer | 97 ml diethanolamine, 800 ml DI H$_2$0, 0.2 g NaN$_3$, 100 mg MgCl$_2$ × 6H$_2$O, DI H$_2$0 to final volume of 1000 ml, pH to 9.8, store at 4° C. in amber bottle |

-continued

| Material | Details |
|---|---|
| Secondary antibodies | Anti-human IgG (γ-chain specific), F(ab')2fragment - Alkaline Phosphatase, produced in goat, affinity isolated antibody (Sigma A3312) |
| Substrate solution | p-Nitrophenyl phosphate solution - 1 mg Sigma S0942 per 1 ml diethanolamine developing buffer |

The following procedure was used:

1. Dilute serotonin 5HT2C receptor to 10 μg/ml in carbonate/bicarbonate coating buffer. Using a multichannel pipet, dispense 50 μl of the antigen solution into each well. Tap the plate gently to make sure the antigen solution is evenly distributed in the wells.

2. Wrap coated plates in plastic wrap and incubate overnight at 4° C. These plates can be stored wrapped in plastic at 4° C. for up to 2 weeks.

3. Using an ELISA plate washer, wash plates by filling all wells five times with PBS/0.05% Tween (wash buffer). Gently tap plates over tissue paper to remove residual wash buffer.

4. Using a multichannel pipet, block the plates by dispensing 100 μl of 1% BSA into all wells. Wrap blocked plates in plastic wrap and incubate for an hour at 37° C.

5. Centrifuge serum samples at 4° C., 10,000 rpm for 10 minutes. Prepare sera dilutions. Initial sera dilution is 1:10 in 1% BSA in PBS. Further 1:2 dilutions in 1% BSA in PBS are made with a final dilution of 1:32000 (or higher if necessary). Four serum samples as well as a positive and negative control, all in duplicates, are run per plate.

6. Wash plate as described in step 3 above.

7. Place 50 μl of diluted serum sample on plate on duplicate wells and 50 μl of 1% BSA on two blank wells. The average OD value obtained from the blank wells will be deducted from the rest of the wells as background. Wrap coated plates in plastic wrap and incubate overnight at 4° C.

8. Wash plate as described in step 3 above.

9. Secondary antibody is diluted 1:1000 in 1% BSA. Using a multichannel pipet add 50 μl of the diluted conjugate to all wells, wrap plate, and incubate for one hour at 37° C.

10. Wash plate as described in step 3 above.

11. Using a multichannel pipet add the substrate solution (50 μl per well). Place on the plate and incubate at room temperature for 120 minutes.

12. Read optical density (OD) at 405 nm immediately after 120 minute incubation.

13. The antibody titer is calculated as the lowest serum dilution reading an OD of 0.10 after 120 minute incubation.

Example 7

Calcium/Calmodulin-Dependent Protein Kinase II (CaM Kinase II) Assay

The Final Assay is based on antibody mediated signaling of neuronal cell line SK-N-SH to induce activation of calcium calmodulin dependent protein kinase II in the neuronal cell line in tissue culture. Dopamine receptors are present on dopaminergic neurons and, when treated with serum antibodies that signal CaM Kinase II, may result in elevated dopamine release. The SignaTECT® Calcium/Calmodulin-Dependent Protein Kinase II (CaM Kinase II) Assay System from Promega Corporation was used.

Cell Line

Human neuroblastoma cell line SK-N-SH (ATCC HTB-11) was cultured in F12-DMEM (Gibco/Invitrogen 12634-082) media supplemented with 10% Fetal Bovine Serum (Hyclone #SH30070.03) and 1% PenStrep (Gibco #15140-122) in tissue culture conditions of 37° C., 5% $CO_2$.

Each patient's serum sample was tested in triplicate. Plate 5×106 SK-N-SH cells overnight in 15 ml of F12-DMEM media in T75 tissue culture flask (VWR BD353136). Next day, pour off medium, preincubate cells (i.e., preload incubation) with 15 ml F12 (Gibco/Invitrogen 11765-047) media supplemented with 2 mM $CaCl_2$, 3 mM KCl and 0.2 mM $MgCl_2$ for 30 min under tissue culture conditions (37° C. in 5% CO2). The basal control was incubated with supplemented F12 media alone. Positive Control=100 mM KCl (i.e., additional KCl added to high salt medium to achieve 100 mM level) and/or a known positive patient at 1:100.

le;.4qAt the end of the 30 minutes preload incubation, decant medium, and then add 10 ml fresh F12 high salt medium (see table below) plus 100 μl of test serum (1:100 dilution). Incubate for 30 minutes in tissue culture incubator. At the end of the this incubation, pour off medium, wash cells 1× with ice-cold PBS (no azide), decant, add an additional 15 ml of ice-cold PBS, and scrap cells off surface of the flask with cell scraper (VWR 353086). Collect the dislodged cells in a clear labeled 15 ml centrifuge tube (VWR 60818-703) and pellet at 4° C. for 15 min at 1500 rpm in a Beckman Allegra 6R Centrifuge.

Carefully remove the PBS from the cells; the cell pellet is not strongly attached to the bottom of the tube. Add 175 μl of protein extraction buffer (with PMSF; see table below) to cell pellet. Homogenize the cell pellet using cold probe homogenizer (Ultra TurraxT8, IKA-Werke) for about 10 seconds on ice—place tubes back on ice. Transfer protein extracts to labeled 1.5 ml Eppendorf tubes (Fisher 05-408-129) and spin at 15000 rpm for 20 min at 4° C. on bench top centrifuge (Prism R, Labnet). Samples should be analyzed immediately using the SignaTECT® CaM KII Assay System II as described below.

The F12 high salt medium and the protein extraction buffer compositions are as follows:

| | |
|---|---|
| F12 High Salt Medium | 50 ml of F12 (serum free) media (Gibco/Invitrogen 1176-047) |
| | 0.1 ml of 1M $CaCl_2$ (final conc. of 2+ mM) |
| | 0.1 ml of 1M KCl (another 2 mM for a final concentration of 5 mM) |
| | 0.02 ml of 1M $MgCl_2$ (another 0.4 mM for a final concentration of 1 mM) |
| Protein Extraction Buffer (store at −20° C.; note that PMSF is added just before use) | 2 ml of 20 mM Tris HCl (pH 8.0) |
| | 0.4 ml of 2 mM EDTA |
| | 0.2 ml of 2 mM EGTA |
| | 200 μl of 1 mg/ml soybean trypsin inhibitor |
| | 100 μl of 10 mg/ml aprotinin |
| | 20 μl of 25 mg/ml leupeptin |
| | 200 μl of 1M DTT |
| | 2.5 ml of 1M benzadin |
| | 17.4 mg of PMF in 1 ml ethanol |
| | $ddH_2O$ to total volume of 100 ml |

The protein extracts are then analyzed using Signa-TECT® CaM KII Assay System II (V8161 Promega) as described below. The CaM Kinase II assay system (sufficient for 96 kinase reactions) includes the following components:
  600 μl ATP, 0.5 mM
  1,400 μl Termination Buffer (2×700 μl)
  300 μl CaM KII Biotinylated Peptide Substrate, 0.5 mM
  1,000 μl CaM KII Reaction 5× Buffer
  500 μl CaM KII Activation 5× Buffer
  500 μl CaM KII Control 5× Buffer
  200 μl Bovine Serum Albumin (BSA, 10 mg/ml)
  1 SAM2® Biotin Capture Membrane.

All system components should be stored at −20° C. where they are stable for up to 6 months. Avoid multiple freeze thaw cycles.

The following required materials include:
  [γ-$^{32}$P]ATP (at 3,000 Ci/mmol, 10 mCi/ml) (Perkin Elmer BLU002A250UC)
  2M NaCl
  2M NaCl in 1% $H_3PO_4$
  enzyme dilution buffer
  30° C. heating block or water bath
  scintillation counter (Beckman Coulter LS 6500)
  washing container
  deionized water
  orbital platform shaker
  37° C. incubator or oven The following procedure was used for the CaM KII assay:

1. Thaw the termination buffer at room temperature, then vortex well. Thaw the rest of the frozen components on ice and vortex gently.

2. Wearing gloves, cut the required number of squares with scissors from the SAM2® Biotin Capture Membrane. Return the unused membrane to the resealable plastic bag at 4° C. for storage of less than one month or at −20° C. for longer periods.

3. Prepare the adenosine triphosphate (ATP) mix by combining, for each reaction, 5 μl of 0.5 mM ATP (unlabeled) with 0.05 μl of [γ-32P]ATP.

4. Prepare the following reactions in 0.5-1.5 ml microcentrifuge tubes:

| Component | Volume/single reaction |
| --- | --- |
| CaM KII Biotinylated Peptide Substrate | 2.5 μl |
| CaM KII Reaction 5X Buffer | 5 μl |
| CaM KII Activation 5X Buffer | 5 μl |
| [γ-$^{32}$P]ATP mix (from Step 3) | 5 μl |
| deionized water | 2.5 μl |

5. Mix the reaction mixture gently and preincubate at 30° C. for 3 minutes. Initiate the reaction by adding 5 μl of the enzyme sample (homogenized cell pellet from above) to the reactants. The total reaction volume will be 25 μl. Incubate at 30° C. for 2 minutes. Terminate the reaction by adding 12.5 μl of termination buffer to the reaction; mix well. The terminated reaction can be kept at room temperature during processing.

6. Spot 25 μl of each sample from the reaction onto prenumbered squares of the SAM2® membrane. Wash and rinse the membranes squares containing samples into a washing container using an orbital platform shaker set on low or by occasional manual shaking as follows:
  (a) wash 1 time for 30 seconds with 200 ml of 2M NaCl;
  (b) wash 3 times for 2 minutes each with 200 ml of 2M NaCl;
  (c) wash 4 times for 2 minutes each with 200 ml of 2M NaCl in 1% $H_3PO_4$;
  (d) wash 2 times for 30 seconds each with 100 ml of deionized water.

Radioactive wash solutions are disposed of according to regulations.

7. The washed membrane squares from step (6) are dried on aluminum foil at about 37° C. until dry (about 15 minutes).

8. To determine specific activity of the [γ-$^{32}$P]ATP, 5 μl of any three of the reactions from step (5) are spotted on separate squares of the SAM2® membrane. These squares are not washed.

9. Each square (from steps 7 and 8) is placed in a labeled scintillation vial (VWR 66022-398) containing 4 ml scintillation fluid (Fisher sx23-5) and capped. Activity is measured using a scintillation counter (Beckman Coulter LS65000 Multi Purpose Scintillation Counter).

10. The specific activity of [γ-$^{32}$P]ATP in cpm/pmol is determined as follows:

$$\text{Specific activity} = \frac{(37.5/5)(X)}{2,500}$$

where 37.5 is the total volume (i.e., reaction volume (25 μl) plus termination buffer volume (12.5 μl); 5 is the volume (5 μl) of the sample in step (8); X is the average counts per minutes of the 5 μl sample (step (8)) as determined in step (9); and 2500 is the amount (in pmol) of ATP in the reaction.

11. The CaM KII enzyme activity in pmol/min/μg protein is determined as follows:

$$\text{Enzyme activity} = \frac{CPM \times (37.5)}{(25) \times (2)(\text{amount of protein in reaction}) \times},$$
(specific activity of [γ-32P]ATP)

where CPM is the scintillation counts per minute of sample from step (7) as determined I step (9); 37.5 is the total volume (i.e., reaction volume (25 μl) plus termination buffer volume (12.5 μl); 25 is the volume in μl of the sample; 2 is the incubation time in minutes of step (5); amount of protein in reaction is determined as described below); and specific activity of [γ-$^{32}$P]ATP is a determined in step 10.

12. The amount of protein for each sample is determined using a Bradford Protein Assay using a Dynex plate reader with an optical density filter of 630 nm.

Example 8

The results for each of the assays used in the present invention are compared to results for a normal and healthy population of children of matched ages and sex of typical PANS/PANDAS patients. The table below summarizes the results based on blood serum samples for such normal populations:

| Assay | Population Size | Mean | Standard Deviation |
| --- | --- | --- | --- |
| 1 (anti-lysoganglioside antibody | 17 | 147 | 80 |
| 2 (anti-tubulin antibody) | 16 | 609 | 288 |

-continued

| Assay | Population Size | Mean | Standard Deviation |
|---|---|---|---|
| 3 (anti-dopamine D1 antibody) | 18 | 1056 | 566 |
| 4 (anti-dopamine D2 antibody) | 18 | 6000 | 5041 |
| 5 (anti-serotonin 5HT2A antibody) | 25 | 2780 | 3225 |
| 6 (anti-serotonin 5HT2C antibody) | 23 | 3043 | 2340 |
| Final (CaM Kinase II Antibody Signaling) | 32 | 94 | 10 |

For Assays 1-6, the mean is reported as the antibody titer (unit-less) calculated as the lowest serum dilution having an optical density of 0.10 at 405 nM after 120 minute incubation (step 13) using the methods described in Examples 1-6, respectively, above. For the Final Assay, the mean is expressed as percentage above basal level of calcium calmodulin dependent protein kinase II enzyme as measured in units of enzyme/mg of protein (specific activity); the value is then calculated as follows:

$$Result = \frac{\left(\text{specific activity of patient sample} - \text{specific activity of blank sample}\right) \times 100}{\text{specific activity of blank sample}}$$

Example 9

The results presented in the table below provided data from the assays for patients possibly having PANDAS using Assays 1 through 4 and the Final Assay. The results were determined using the protocols described in Examples 1-4 and Example 7, respectively. The results for Assays 1-4 and the Final Assay were compared to populations of normal patients as provided in Example 8.

| | | | Results | | |
|---|---|---|---|---|---|
| Patient | Assay 1 | Assay 2 | Assay 3 | Assay 4 | Final Assay |
| 1 | 640 | 1000 | 2000 | 32,000 | 189 |
| 2 | 80 | 500 | 8000 | 4000 | 168 |
| 3 | 320 | 8000 | 2000 | 8000 | 145 |
| 4 | 640 | 1000 | 8000 | 4000 | 210 |
| 5 | 1280 | 500 | 8000 | 4000 | 175 |
| 6 | 160 | 500 | 1000 | 2000 | 160 |
| 7 | 1280 | 1000 | 8000 | 4000 | 120 |
| 8 | 320 | 8000 | 2000 | 4000 | 115 |
| 9 | 160 | 1000 | 8000 | 16,000 | 115 |
| 10 | 80 | 250 | 1000 | 2000 | 110 |
| 11 | 80 | 500 | 1000 | 4000 | 95 |
| 12 | 160 | 1000 | 1000 | 4000 | 100 |

Patients 1-6 were found "highly likely" to have PANDAS/PANS; patients 7-9 were found "likely" to have PANDAS; and patients 10-12 were found "not likely" to have PANDAS/PANS.

APPENDIX

Representative References

Husby, G., I. van de Rijn, J. B. Zabriskie, Z. H. Abdin, and R. C. Williams. 1976. "Antibodies reacting with cytoplasm of subthalamic and caudate nuclei neurons in chorea and acute rheumatic fever." J. Exp. Med. 144: 1094-1110.

Bronze, M. S., and J. B. Dale. 1993. "Epitopes of streptococcal M proteins that evoke antibodies that cross-react with human brain." J. Immunol. 151:2820-2828.

Kurlan, R. 1998. "Tourette's syndrome and 'PANDAS': Will the relation bear out? Pediatric autoimmune neuropsychiatric disorders associated with streptococcal infection." Neurology 50(6): 1530-4.

Perlmutter, S. J., S. F. Leitman, M. A. Garvey, S. Hamburger, E. Feldman, H. L. Leonard, and S. E. Swedo, 1999 "Therapeutic plasma exchange and intravenous immunoglobulin for obsessive-compulsive disorder and tic disorders in childhood." Lancet 354: 1153-58.

Church, A. J., F. Cardoso, et al. 2002. "Anti-basal ganglia antibodies in acute and persistent Sydenham's chorea." Neurology 59(2): 227-31.

Church, A. J., R. C. Dale, et al. 2003. "Tourette's syndrome: A cross sectional study to examine the PANDAS hypothesis." J. Neurol. Neurosurg. Psychiatry 74(5): 602-7.

Dale, R. C., A. J. Church, et al. 2003. "Striatal encephalitis after varicella zoster infection complicated by tourettism." Movement Disorders 18(12): 1554-6.

Shet, A., E. L. Kaplan, D. R. Johnson, and P. P. Cleary. 2003. "Immune Response to Group A Streptococcal C5a Peptidase in Children: Implications for Vaccine Development." J. Infec. Dis. 188:809-17.

Singer, H. S. and C. Loiselle 2003. "PANDAS: A commentary." J. Psychosom. Res. 55(1): 31-9.

Singer, H. S., C. R. Loiselle, et al. 2003. "Anti-basal ganglia antibody abnormalities in Sydenham chorea." J Neuroimmunol. 136(1-2): 154-61.

Church, A. J., R. C. Dale, and G. Giovannoni. 2004. "Anti-basal ganglia antibodies: a possible diagnostic utility in idiopathic movement disorders?" Arch. Dis. Child. 89:611-614.

Kirvan, C. A., S. E. Swedo, J. S. Heuser, and M. W. Cunningham. 2003. "Mimicry and autoantibody-mediated neuronal cell signaling in Sydenham chorea." Nature Medicine 9: 914-920.

Kurlan, R. 2004. "The PANDAS hypothesis: Losing its bite?" Movement Disorders 19(4): 371-4.

Kurlan, R. and E. L. Kaplan 2004. "The pediatric autoimmune neuropsychiatric disorders associated with streptococcal infection (PANDAS) etiology for tics and obsessive-compulsive symptoms: Hypothesis or entity? Practical considerations for the clinician." Pediatrics 113 (4): 883-6.

Loiselle, C. R., O. Lee, et al. 2004. "Striatal microinfusion of Tourette syndrome and PANDAS sera: Failure to induce behavioral changes." Movement Disorders 19(4): 390-6.

Snider, L. A. and S. E. Swedo. 2004. "PANDAS: current status and directions for research." Molecular Psychiatry 9: 900-907.

Dale, R. C., P. M. Candler, et al. 2005. "Neuronal surface glycolytic enzymes are autoantigen targets in post-streptococcal autoimmune cns disease." J. Neuroimmunol. 172(1-2): 187-197.

Singer, H. S., J. J. Hong, et al. 2005. "Serum autoantibodies do not differentiate PANDAS and Tourette syndrome from controls." Neurology 65: 1701-1707.

Kirvan, C. A., Swedo, S. E., Snider, L. A., and M. W. Cunningham. 2006. "Antibody-mediated neuronal cell signaling in behavior and movement disorders." J. Neuroimmunol. 179: 173-179.

Kirvan, C. A., S. E. Swedo, D. Kurahara, and M. W. Cunningham. 2006. "Streptococcal mimicry and antibody-mediated cell signaling in the pathogenesis of Sydenham's chorea". Autoimmunity 39: 21-29.

Kirvan, C. A., C. J. Cox, S. E. Swedo, and M. W. Cunningham. 2007. "Tubulin is a neuronal target of autoantibodies in Sydenham's chorea". J. Immunol. 178: 7412-7421.

Kurlan, R., D. Johnson, et al. 2008. "Streptococcal infection and exacerbations of childhood tics and obsessive-compulsive symptoms: A prospective blinded cohort study." Pediatrics 121(6): 1188-97.

Singer, H. S., C. Gause, et al. 2008. "Serial immune markers do not correlate with clinical exacerbations in pediatric autoimmune neuropsychiatric disorders associated with streptococcal infections." Pediatrics 121(6): 1198-205.

Bombaci, M., R. Grifantini, M. Mora, V. Reguzzi, R. Petracca, E. Meoni, S. Balloni, C. Zingaretti, F. Falugi, A. G. O. Manetti, I. Margarit, J. M. Musser, F. Cardona, G. Orefici, G. Grandi, G. Bensi. 2009. "Protein array profiling of tic patient sera reveals a broad range and enhanced immune response against group a streptococcus antigens." PLoS ONE 4(7): e6332. doi:10.1371/journal.pone.0006332.

Brilot, F., V. Merheb, et al. 2011. "Antibody binding to neuronal surface in Sydenham chorea, but not in PANDAS or Tourette syndrome." Neurology. 76:1-6 (Published ahead of print on Mar. 16, 2011, at www.neurology.org).

Leckman, J., R. A. King, et al. 2011. "Streptococcal upper respiratory tract infections and exacerbations of tic and obsessive-compulsive symptoms: A prospective longitudinal study." J. Am. Acad. Child. Adolesc. Psychiatry 50(2): 108-118.

Lewin, A. B., E. A. Storch, P. J. Mutch, and T. K. Murphy. 2011. "Neurocognitive Functioning in Youth With Pediatric Autoimmune Neuropsychiatric Disorders Associated With Streptococcus." J. Neuropsychiatry Clin. Neurosci. 23:391-398.

Ben-Pazi, H., and O. Sadan, et al. 2012. "Striatal microinjection of Sydenham chorea antibodies: Using a rat model to examine the dopamine hypothesis." J. Mol. Neurosci. 46(1):162-6.

Brimberg, L., I. Benhar, A. Mascaro-Blanco, K. Alvarez, C. Winter, J. Klein, A. E. Moses, F. Somnier, J. Leckman, S. Swedo, M. W. Cunningham, and D. Joel. 2012. "Behavioral immunological and neural abnormalities antibodies. Implications in pediatric autoimmune neuropsychiatric disorders associated with streptococci." Neuropsychopharmacology 37:2076-2087.

Dale, R. C., V. Merheb, et al. 2012. "Antibodies to surface dopamine-2 receptor in autoimmune movement and psychiatric disorders." Brain 135(11): 3453-68.

Murphy, T. K., E. A. Storch, A. B. Lewin, P. J. Edge, and W. K. Goodman. 2012. "Clinical Factors Associated with Pediatric Autoimmune Neuropsychiatric Disorders Associated with Streptococcal Infections." J. Pediatr. 160:314-9.

Singer, H. S., D. L. Gilbert, et al. 2012. "Moving from PANDAS to CANS." J. Pediatr. 160(5): 725-31.

Swedo, S. E., J. F. Leckman, and N. R. Rose. 2012. "From Research Subgroup to Clinical Syndrome: Modifying the PANDAS Criteria to describe PANS (pediatric acute-onset neuropsychiatric syndrome)." Pediatr. Therapeut. 2:113 (doi:10.4172/2161-0665.1000113).

What is claimed is:

1. A method of analyzing a sample from a patient, comprising:
   a) providing a surface comprising a lysoganglioside, tubulin, dopamine receptor D1, and dopamine receptor D2 immobilized thereon;
   b) contacting the surface with the sample to form an anti-lysoganglioside antibody/lysoganglioside complex, an anti-tubulin antibody/tubulin complex, an anti-dopamine receptor D1 antibody/dopamine receptor D1 complex, and an anti-dopamine receptor D2 antibody/dopamine receptor D2 complex on the surface;
   c) measuring an antibody titer of each of anti-lysoganglioside antibody, anti-tubulin antibody, anti-dopamine receptor D1 antibody, and anti-dopamine receptor D2 antibody;
   d) providing an assay for measuring calcium/calmodulin-dependent protein kinase II (CaM Kinase II) activity;
   e) contacting the assay for measuring CaM Kinase II activity with the sample; and
   f) measuring CaM Kinase II activity.

2. The method of claim 1, wherein one or more assay plates comprises said surface.

3. The method of claim 2, wherein the one or more assay plates is one or more microtiter plates.

4. The method of claim 2, wherein the one or more assay plates each separately comprises one of the lysoganglioside, tubulin, dopamine receptor D1, and dopamine receptor D2.

5. The method of claim 1, wherein the sample is serum obtained from blood.

6. The method of claim 1, wherein the sample is obtained from cerebrospinal fluid.

7. The method of claim 1, wherein the lysoganglioside is lysoganglioside GM1.

8. A method of analyzing a sample from a patient, comprising:
   a) providing an assay plate having a portion coated with a lysoganglioside, a portion coated with tubulin, a portion coated with dopamine receptor D1, and a portion coated with dopamine receptor D2;
   b) applying a first portion of the sample to the portion of the assay plate coated with the lysoganglioside, forming an antilysoganglioside antibody/lysoganglioside complex thereon;
   c) applying a second portion of the sample to the portion of the assay plate coated with tubulin, forming an anti-tubulin antibody/tubulin complex thereon;
   d) applying a third portion of the sample to the portion of the assay plate coated with dopamine receptor D1, forming an anti-dopamine receptor D1 antibody/dopamine receptor D1 complex thereon;
   e) applying a fourth portion of the sample to the portion of the assay plate coated with dopamine receptor D2, forming an anti-dopamine receptor D2 antibody/dopamine receptor D2 complex thereon;
   f) measuring an antibody titer of each of anti-lysoganglioside antibody, anti-tubulin antibody, anti-dopamine receptor D1 antibody, and anti-dopamine receptor D2 antibody;
   g) providing an assay for measuring calcium/calmodulin-dependent protein kinase II (CaM Kinase II) activity;

h) applying a fifth portion of the sample to the assay for measuring CaM Kinase II activity; and
i) measuring CaM Kinase II activity.

9. The method of claim 8, wherein the sample is serum obtained from blood.

10. The method of claim 8, wherein the sample is obtained from cerebrospinal fluid.

11. The method of claim 8, wherein the lysoganglioside is lysoganglioside GM1.

12. A method of analyzing a sample from a patient, comprising:
   a) providing a first assay plate having a portion coated with lysoganglioside GM1;
   b) applying a first portion of the sample to the portion of the first assay plate coated with lysoganglioside GM1, forming an anti-lysoganglioside antibody/lysoganglioside complex thereon;
   c) measuring an antibody titer of anti-lysoganglioside antibody;
   d) providing a second assay plate having a portion coated with tubulin;
   e) applying a second portion of the sample to the portion of the second assay plate coated with tubulin, forming an anti-tubulin antibody/tubulin complex thereon;
   f) measuring an antibody titer of anti-tubulin antibody;
   g) providing a third assay plate having a portion coated with dopamine receptor D1;
   h) applying a third portion of the sample to the portion of the third assay plate coated with dopamine receptor D1, forming an anti-dopamine receptor D1 antibody/dopamine receptor D1 complex thereon;
   i) measuring an antibody titer of anti-dopamine receptor D1 antibody;
   j) providing a fourth assay plate having a portion coated with dopamine receptor D2;
   k) applying a fourth portion of the sample to the portion of the fourth assay plate coated with dopamine receptor D2, forming an anti-dopamine receptor D2 antibody/dopamine receptor D2 complex thereon;
   l) measuring an antibody titer of anti-dopamine receptor D2 antibody;
   m) providing an assay for measuring calcium/calmodulin-dependent protein kinase II (CaM Kinase II) activity;
   n) applying a fifth portion of the sample to the assay for measuring CaM Kinase II activity; and
   o) measuring CaM Kinase II activity.

13. The method of claim 12, wherein the sample is serum obtained from blood.

14. The method of claim 12, wherein the sample is obtained from cerebrospinal fluid.

\* \* \* \* \*

UNITED STATES PATENT AND TRADEMARK OFFICE
CERTIFICATE OF CORRECTION

PATENT NO. : 9,804,171 B2  
APPLICATION NO. : 15/045146  
DATED : October 31, 2017  
INVENTOR(S) : Phina Madeleine Cunningham Page 1 of 2

It is certified that error appears in the above-identified patent and that said Letters Patent is hereby corrected as shown below:

On the Title Page

Item (57), (Abstract) at Line 14, Change "tiers" to --titers--.

In the Specification

In Column 6 at Line 42, Change "lysoganglio side," to --lysoganglioside,--.

In Columns 13-14 at Line 9, Change "$H_20$," to --$H_2O$,--.

In Columns 13-14 at Line 10, Change "$H_20$" to --$H_2O$--.

In Column 13 at Line 42, Change "above)." to --above.--.

In Columns 15-16 at Line 9, Change "$H_20$," to --$H_2O$,--.

In Columns 15-16 at Line 10, Change "$6H_20$," to --$6H_2O$,--.

In Columns 15-16 at Line 10, Change "$H_20$" to --$H_2O$--.

In Column 15 at Line 42 (approx.), Change "above)." to --above.--.

In Columns 17-18 at Line 9, Change "$H_20$," to --$H_2O$,--.

In Columns 17-18 at Line 10, Change "$6H_20$," to --$6H_2O$,--.

In Columns 17-18 at Line 10, Change "$H_20$" to --$H_2O$--.

In Columns 19-20 at Line 6, Change "$H_20$" to --$H_2O$--.

Signed and Sealed this  
Thirty-first Day of July, 2018

Andrei Iancu  
*Director of the United States Patent and Trademark Office*

CERTIFICATE OF CORRECTION (continued)
U.S. Pat. No. 9,804,171 B2

In Columns 19-20 at Line 7, Change "$H_20$" to --$H_2O$--.

In Columns 21-22 at Line 3, Change "$H_20$" to --$H_2O$--.

In Columns 21-22 at Line 4, Change "$H_20$" to --$H_2O$--.

In Column 21-22 at Line 67, Change "$H_20$" to --$H_2O$--.

In Columns 21-22 at Line 68, Change "$H_20$" to --$H_2O$--.

In Column 24 at Line 31, Change "the this" to --this--.